(12) United States Patent
Ruiz et al.

(10) Patent No.: US 8,176,766 B1
(45) Date of Patent: May 15, 2012

(54) LIQUID AND SOLID TRAPPING MOUTHPIECE

(75) Inventors: Hector Ruiz, Olivette, MO (US); Ildefonso Gonzalez, St. Charles, MO (US); Keith Lueck, Fenton, MO (US)

(73) Assignee: Alcotek, Inc., St. Louis, MO (US)

( * ) Notice: Subject to any disclaimer, the term of this patent is extended or adjusted under 35 U.S.C. 154(b) by 493 days.

(21) Appl. No.: 12/408,451

(22) Filed: Mar. 20, 2009

Related U.S. Application Data

(60) Provisional application No. 61/039,816, filed on Mar. 27, 2008.

(51) Int. Cl.
*G01N 1/22* (2006.01)
*G01N 33/497* (2006.01)

(52) U.S. Cl. .......................................... 73/23.3; 422/84
(58) Field of Classification Search ................... 73/23.3; 422/84
See application file for complete search history.

(56) References Cited

U.S. PATENT DOCUMENTS

| | | | | |
|---|---|---|---|---|
| 1,170,438 A * | 2/1916 | Fahrney | ............................ | 55/337 |
| 3,013,628 A * | 12/1961 | Jacobs et al. | .................. | 422/173 |
| 3,070,990 A * | 1/1963 | Krinov | .......................... | 73/23.31 |
| 3,564,843 A * | 2/1971 | Hirshcler, Jr. et al. | .......... | 60/311 |
| 3,780,567 A * | 12/1973 | Ovard | ........................ | 73/863.21 |
| 3,853,512 A * | 12/1974 | Hayashi | ............................ | 96/59 |
| 4,668,257 A * | 5/1987 | van der Meer et al. | ....... | 55/434.1 |
| 4,868,545 A * | 9/1989 | Jones | .......................... | 340/573.1 |
| 4,969,494 A * | 11/1990 | Chefson | .......................... | 141/93 |
| 5,123,945 A * | 6/1992 | Lin | ................................ | 55/395 |
| 5,215,553 A * | 6/1993 | Herman et al. | ................. | 95/269 |
| 5,238,472 A * | 8/1993 | Pfister et al. | ................. | 55/282.3 |
| 5,254,147 A * | 10/1993 | Finke | ............................... | 55/337 |
| 5,321,972 A * | 6/1994 | Stock | ............................. | 73/23.2 |
| 5,496,394 A * | 3/1996 | Nied | ............................... | 95/271 |
| 5,826,575 A * | 10/1998 | Lall | ........................ | 128/205.12 |
| 5,918,259 A * | 6/1999 | Squirrell | ........................ | 73/28.01 |
| 6,042,628 A * | 3/2000 | Nishikiori et al. | ............. | 55/337 |
| 6,103,534 A * | 8/2000 | Stenger et al. | ................... | 436/63 |
| 6,170,342 B1 * | 1/2001 | John | ........................... | 73/863.21 |
| 6,270,545 B1 * | 8/2001 | Lee et al. | ........................ | 55/345 |
| 6,685,759 B2 * | 2/2004 | Dahlin et al. | ................... | 55/465 |
| 6,932,082 B2 * | 8/2005 | Stein | ......................... | 128/200.22 |
| 7,101,340 B1 * | 9/2006 | Braun | ............................ | 73/23.3 |
| 7,140,068 B1 * | 11/2006 | Vander Baan et al. | .......... | 15/347 |
| 7,377,901 B2 * | 5/2008 | Djupesland et al. | ........... | 73/23.3 |
| 7,708,808 B1 * | 5/2010 | Heumann | ........................ | 95/271 |
| 7,779,840 B2 * | 8/2010 | Acker et al. | ............. | 128/204.16 |
| 2009/0158932 A1 * | 6/2009 | Arnold | ............................ | 95/271 |

* cited by examiner

*Primary Examiner* — Lisa Caputo
*Assistant Examiner* — Punam Roy
(74) *Attorney, Agent, or Firm* — Lewis, Rice & Fingersh, L.C.

(57) ABSTRACT

A liquid and solid trap which induces cyclonic motion of a breath flow to separate solids and liquids from a breath sample prior to that sample being provided to a breath detector for determining composition of the vapor portion of said sample. The trap is generally used on delivery type testing devices used for measuring breath alcohol content.

18 Claims, 5 Drawing Sheets

LIQUID AND SOLID TRAPPING MOUTHPIECE

CROSS REFERENCE TO RELATED APPLICATION(S)

This application claims the benefit of U.S. Provisional Patent Application Ser. No. 61/039,816, filed Mar. 27, 2008 the entire disclosure of which is herein incorporated by reference.

BACKGROUND

1. Field of the Invention

The present invention relates to systems and methods for the trapping of liquids or solids which may be present in a breath prior to the breath being presented to a breath testing device.

2. Description of the Related Art

For the purposes of public safety on the roads and elsewhere, there is a need to make sure that individuals are not operating potentially dangerous machines (such as automobiles) while they are impaired by the effects of alcohol consumption. To try and prevent people from driving drunk, most states have enacted laws which impose fines or other criminal penalties if individuals have a breath or blood alcohol level above a certain amount. In order to effectively enforce these laws, it is necessary to be able to measure the alcohol concentration of a human's breath and compare the results against legal limits. There are a variety of measuring instruments used for determining the concentration of alcohol in human breath ranging from small hand held devices to larger bench top units and machines built into cars or certain machinery. Since a determination of breath alcohol above the legal threshold can result in criminal penalties, loss of a job, or other sanctions, the accuracy of these instruments is paramount.

In addition to accuracy, there are also obvious concerns about the sanitation and reliability of evidentiary breath testers. Since the machines need to take a sample of the subject's breath, they are necessarily exposed to whatever else may be in the subject's breath or mouth at the time the measurement is taken. Liquid droplets or solid particles which may be in the breath can present a myriad of problems for an evidentiary breath tester. Specifically, they can result in unsanitary conditions if they remain in the breath tester and could potentially be inhaled by a later subject. They can also result in microbial growth or other fouling of the testing instrument's sampling mechanism. Similarly, if such particles get into the testing chamber of the tester, they can potentially damage the chamber or make the tester require service in order to remove the contamination and ensure that the device operates in a reliable and accurate manner.

A breath sample generally cannot to be taken without the human subject cooperating. Specifically, the human subject generally must provide the sample of breath for analysis, generally by exhalation into the breath testing apparatus. This is usually done in the form of a "blow" by the subject, i.e. a forced exhalation against backpressure into a tube or manifold. From the breath in the tube, a sample is then taken by the tester in order to determine the alcohol concentration in the subject's breath.

Generally, the portion of this tube that enters the subject's mouth is generally a low cost, replaceable, and disposable mouthpiece. The device is disposable for sanitary reasons so that there is a reduced chance of germs, or other undesirable components of a subject's breath, being transferred between different people. It is low cost and replaceable to meet the requirements of being affordable for regular use of the breath tester when the breath tester is to be used on multiple subjects.

Depending on the type of breath testing apparatus used, some tubes or devices may contain check valves that keep a subject from sucking back air from the tube. This check valve can provide for improved sanitation by inhibiting the subject from pulling air, and any suspended material, from the testing device. Certain devices may also have check valves to provide for increased accuracy as alteration in the nature or speed of the flow could produce an inaccurate result and to inhibit the subject from trying to fool the machine by pulling fresh air through the machine and into their lungs or reducing a sample size by pulling back on a sample, instead of fully exhaling into the machine.

Most breath testing devices utilize exhaled breath vapor, and specifically deep lung vapor (alveolar breath), to determine breath alcohol level. This breath vapor generally presents an accurate representation of blood alcohol level and therefore is most desired in breath testing. However, to obtain such a deep lung breath, a human user needs to generally breathe a significant amount of air into the tube (so as to clear air from the mouth and upper lungs) and as part of doing so will often force liquid or solid particles into the tube as well due to the force of the breath. This can include liquid droplets of saliva or other materials in the mouth or throat or particles of food or other solid substances.

These problems can be further exaggerated in inebriated subjects as when they blow into alcohol breath testers, there is an increased propensity for saliva, in the form of drool or slobber, to be delivered along with the breath during a subject blow. This can both increase the likelihood that some material is projected, as well as the total amount of material projected for an average subject. Sometimes, inebriated subjects, who have impaired thinking, will even try to blow spit, phlegm, nasal fluids, or solids into a breath tester, thinking that this might affect the instrument in some way that will be of benefit to themselves. A very inebriated subject may even inadvertently vomit or otherwise project certain stomach contents into the tube.

Traditionally in certain types of testing devices, the tube has done very little to prevent these problems as they have very little effect on most sampling devices. In machines where liquid or solid projection can cause increased problems, certain types of spit traps do exist. FIG. 1 provides an example of mouthpiece spit trap design of the prior art consisting of various "baffle" structures. These are meant to provide a more tortuous path for the breath and include surfaces that are meant to frictionally hold back liquids and solids, or create eddies to trap liquids, all the while letting vapor pass through. These designs are effective to an extent, but only at lower breath flow rates. At higher flow rates, these mouthpieces often perform poorly as the stronger breath tends to sweep particles and droplets along with it due to the increased pressure it provides.

As a result, measuring instruments utilizing such spit valves are often designed with internal restrictions designed to increase backpressure during a subject blow and therefore purposely keep flow rates low, thus increasing the effectiveness of the baffle-type mouthpiece designs to serve as traps. The problem with this is that these instruments become "hard to blow" as subjects have to blow hard against this backpressure and it can become quite uncomfortable and unnatural for the subject.

Especially when a subject is potentially inebriated, one prefers not to introduce factors into the process that make it more difficult to get a proper breath sample and therefore designs which increase backpressure can be considered to simply trade one problem for the other. While they may reduce material projection into the device, they may simultaneously have the user produce a less desirable sample breath or have trouble producing a useable sample at all. Because backpressure changes can create problems, there are internal bodies that regulate the maximum backpressure allowed in a measuring instrument. However, these regulations generally only regulate the maximum backpressure which can be used in any instrument to make sure that the instrument will obtain a reasonable sample. Individual manufacturers may use any backpressure up to this amount and, therefore, there may be different backpressures between different devices. So, in the case of universal mouthpieces which are deigned to operate on a variety of different instruments where manufacturers may internally select to use different backpressures to provide for their own internal accuracy, these have to be designed to operate across a variety of instruments with a variety of backpressures. In the case of baffle systems such as that of FIG. 1, this can lead to a mouthpiece which is effective with one device, but ineffective in another.

SUMMARY

Because of these and other problems in the art, described herein, among other things, is a breath tester for trapping particles, the tester comprising: a trap including: an inverted generally conical frustum having a top and a bottom where the diameter of the top is greater than the diameter of the bottom; an inlet port arranged toward the top of the frustum, for having a breath flow enter the frustum and form a cyclone therein; and an exit port arranged at the top for exhausting breath flow from the conical frustum; a sample inlet port for accepting a sample of the exhausted breath vapor from the exit port; and a detector, which can determine the alcohol concentration of the sample.

In an embodiment of the tester the detector may be a fuel cell or may utilize infrared absorption.

In an embodiment of the tester the tester is a delivery tester.

In an embodiment of the tester the breath flow is produced by a human being.

In an embodiment of the tester the breath flow is directly provided to the detector.

In an embodiment of the tester liquid suspended in the breath flow at least partially condenses from the breath flow on an inner surface of the frustum.

In an embodiment of the tester the trap is disposable after each use or reusable for multiple uses.

In an embodiment of the tester the exit port is generally centered in the top

In an embodiment of the tester the trap further comprises baffles inside the inverted conical frustum which may be generally circular or generally helical.

There is also described herein a method of providing a breath stream for breath alcohol analysis, the method comprising: having a user breathe a breath flow into an input tube; inducing a cyclone on the breath flow within a trap; utilizing the cyclone to expel at least some solid particles and liquid droplets from the breath flow; expelling the breath flow from the trap while capturing the particles and droplets in the trap; and providing the expelled breath flow to a breath alcohol testing device.

In an embodiment of the method the breath alcohol testing device is a delivery type of device.

In an embodiment of the method the breath alcohol testing device utilizes infrared absorption on the expelled breath flow.

In an embodiment of the method the trap comprises an inverted conical frustum which may further comprises baffles.

There is also described herein a breath alcohol tester comprising: an input tube for obtaining a breath flow; means for inducing cyclonic motion in the breath flow to expel at least some solid particles and liquid droplets from the breath flow; a trap for capturing the particles and droplets; and an exhaust for providing breath flow from the trap to a breath alcohol testing device.

In an embodiment of the tester the input tube interfaces with a disposable mouthpiece.

DESCRIPTION OF PREFERRED EMBODIMENT(S)

In the field of breath testing devices, testing devices are generally of two distinct types depending on how the associated breath tester is designed to sample the breath. With these two different devices come different types of mouthpieces which are designed to focus the breath in different ways to make sure that the breath vapor is provided to the sampling port of the device in the desired fashion.

The first type of device is a sampling device where the mouthpiece is used with a breath tester which is deigned to take a small sample of exhaled breath for testing. These mouthpieces are generally temporarily mounted directly on the measuring instrument, and serve as a temporary manifold for the measuring instrument. They flow air over a testing port and the port will take a small sample from the air stream.

Figure 1:
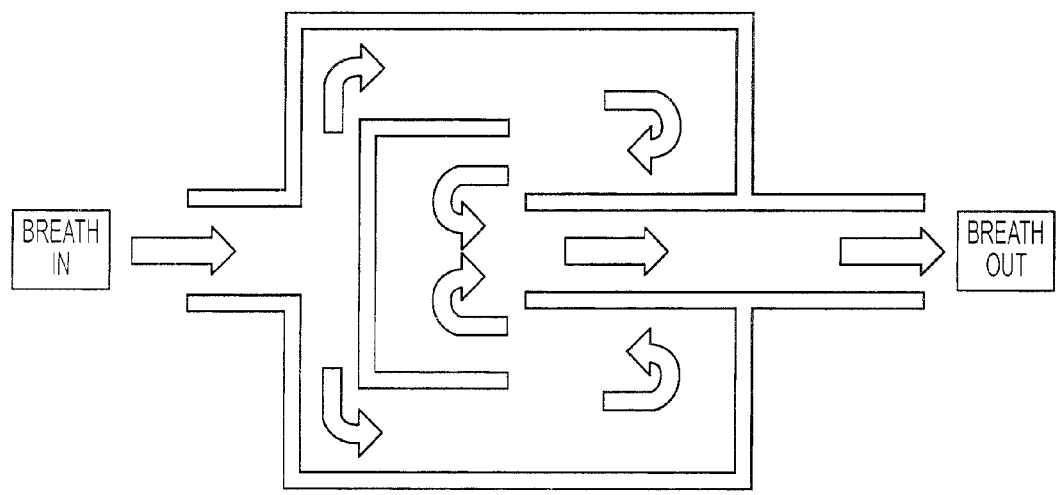
FIG. 1 shows a cross sectional view of a prior art delivery mouthpiece utilizing a baffle design.
Figure 2:
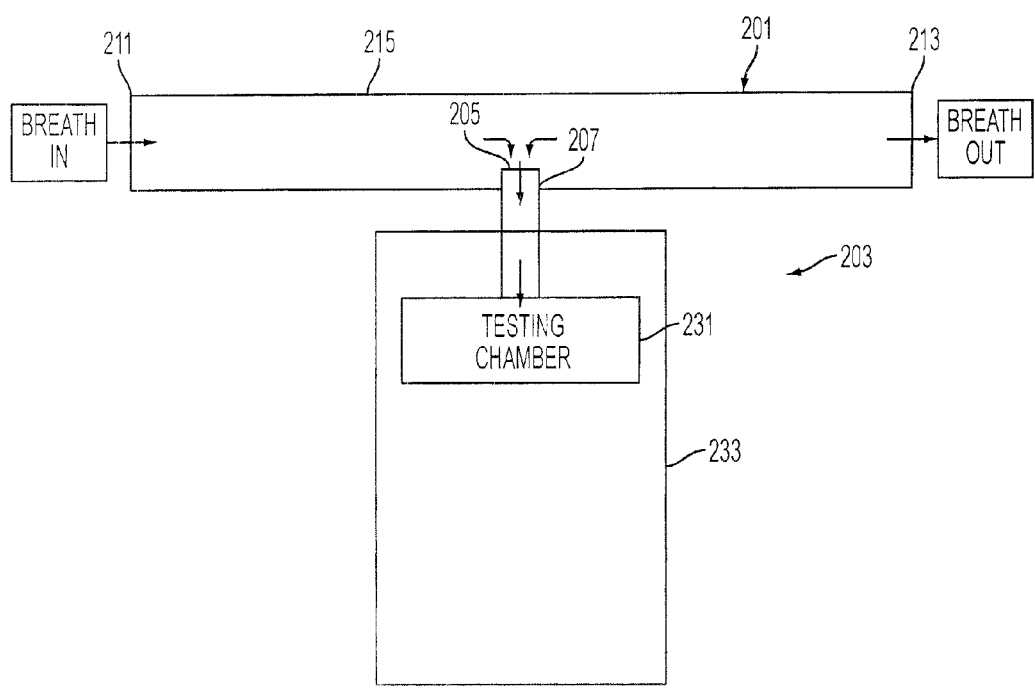
FIG. 2 shows an embodiment of a prior art sampling type of breath testing device with an attached mouthpiece.

FIG. 2 shows an example of a typical sampling mouthpiece (201) in place on a typical sampling instrument (203). Generally, an instrument sampling port (205) protrudes into a hole (207) in the side of the mouthpiece (201). The port (205) becomes sealed from conditions outside the mouthpiece (201), other than what is pushed into the mouthpiece (201) from the input end (211) once the mouthpiece (201) is in place. During a subject "blow," the user will place their lips around the extending portion (215) of the mouthpiece and seal their lips to its external surface. The user will then breathe out and breath flows into the input end (211) and out of an output vent (213) of the mouthpiece and into ambient air. At the proper moment (generally selected to obtain a sample of deeper lung breath), a small portion of the breath stream (typically less than 1 cubic centimeter) is pulled in through the port (205) for analysis outside of the mouthpiece (201). This analysis generally occurs in a testing chamber (231) in the main housing (233) of the device (203). Sampling devices (203) often use fuel cell technology or similar instruments to perform their testing.

Figure 3:
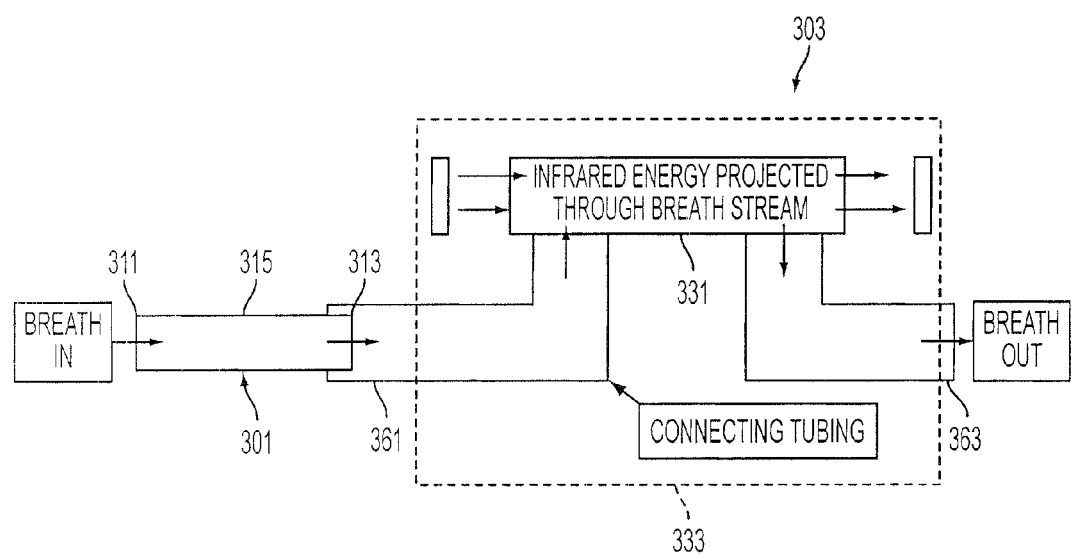
FIG. 3 shows an embodiment of a prior art delivery type of breath testing device including an attached mouthpiece.

Delivery mouthpieces on the other hand connect either directly to an internal instrument manifold or connect to tubing that is, in turn, connected to an internal instrument manifold which is where measurement will actually occur. FIG. 3 shows an example of a delivery mouthpiece (301) in conjunction with a delivery tester (303). This mouthpiece (301) has an outlet (313) that seals against ambient when connected to the instrument (303). In operation of this type of device (303), the user will again place the extending end (315) of the mouthpiece (301) into their mouth and seal their lips around in exterior surface. The user will then breathe into the mouthpiece (301) via the input end (311) of the mouthpiece (301) and the breath passes through the mouthpiece (301) and directly into an input (361) of the measuring instrument (303). The entire breath then enters into the testing chamber (331) where it is tested before it can exit from the testing chamber (331) through an exhaust (363) to ambient. Again, the testing chamber (331) is generally located in the main housing (333) of the device (203).

This type of direct input of the entire breath is generally to facilitate real-time and continuous measurement of the breath alcohol concentration with a technology such as infrared absorption as opposed to simply sampling a small portion of the breath. Since technologies such as infrared absorption generally require a significant volume of breath across which the absorption of infrared energy is measured, larger (and more continuous) samples are preferably provided.

As discussed above, there is a propensity of breath provided to breath testers to have liquids or solids suspended therein which are not useful for the measurement and may be detrimental to the tester (203) or (303). Further, since human breath typically exits the body at around 34° C. and mouthpieces (201) and (301) are typically not heated above ambient for expense reasons, condensation can easily occur on interior surfaces of a mouthpiece (201) or (301) during a breath since it will almost always be colder than the breath placed therein. In addition to suspended particles and liquids, there is also the possibility that this condensed liquid can be caught up in a future portion of the breath stream and be delivered along with the breath vapor to the instrument (203) or (303).

It should be obvious that sampling mouthpieces (201) without spit traps don't represent quite the level of hazard as delivery mouthpieces (301) without spit traps to a measuring instrument (203) or (303). Looking at FIG. 2, with a sampling mouthpiece (201) almost all the breath, and whatever else it might carry with it, exits the mouthpiece (201) into ambient without entering the testing chamber. Therefore, there is only a very small chance, at the time of sample, that these foreign materials could enter the testing chamber (231). Further, even if there any residues left on the mouthpiece (201), it is designed to be discarded after the test and the sampling port (205) is so comparatively small that it has a relatively minimal chance of having materials remain on or within it.

Looking at FIG. 3, it should also be apparent that delivery mouthpieces (301) are part of a system where virtually all the breath must pass through the testing chamber (331). Therefore if that breath is also carrying foreign liquids and solids, there is a chance of leaving residues along the length of internal structure between entrance (361) and exit (363) ports and in the testing chamber (331) itself with every test. Such residues can remain in the instrument (303) even after the breath test is complete and the mouthpiece (301) is discarded.

Owners and operators of breath testing instruments generally prefer that only breath vapor enters the testing chamber (231) or (331) of the measuring instrument (203) or (303). The presence of liquids and/or solids in the breath provided by the present subject in any given test are not much of an immediate problem because these substances are roughly in equilibrium with the breath of the present sample. Therefore, the presence of such liquids or solids in the testing chamber (231) or (331) generally does not effect the device's accuracy in the breath alcohol determination. However, should these materials remain in the testing instrument (203) or (303) after the test is completed, they can wreak havoc with the instrument (203) or (303).

Residues which remain in the testing system can force an instrument (203) or (303) to be taken out of service because it can longer perform proper blank tests (that is, it can no longer accurately re-zero) between subjects because the presence of the material in the testing chamber creates a false reading. Similarly, a device (203) or (303) with foreign material remaining in the testing chamber (231) or (331) may no longer be able to properly analyze a test gas and therefore will fail accuracy check procedures because testing chamber (231) or (331) is contaminated by the presence of the foreign material. Similarly, presence of foreign matter can also degrade the sensor signal affecting measurement, making the device (203) or (303) unable to complete a determination of alcohol percentage. Even if material is not in the testing chamber (231) or (331), material in the air pathway can serve to disrupt the air flow or reduce the amount of breath which can flow into the machine. Similarly, microorganisms which may be on the material may ultimately create a bigger piece of material over time. Still further, such material in its own decomposition, may give off gases or vapors which could lead to a false reading.

Because of these types of concerns, instruments generally have safeguards where the testing instrument (203) or (303) is designed to detect that it has become fouled and prevent further testing with the faulty instrument (203) or (303). Thus, inaccurate breath alcohol determinations are generally not given. However, an instrument (203) or (303) which has become fouled generally must be removed from service and replaced with another instrument (203) or (303) while it is being disassembled, cleaned, and re-calibrated since it will be unusable until the problem has been removed. This can be very costly in both time, while the instrument (203) or (303) is down and unusable, and in having to own backup instruments (203) or (303) that can be used while the first is being repaired.

There are a wide variety of mouthpieces (201) or (301) in the market. Some are designed specifically for certain instruments while others are designed as universal mouthpieces to work with a large variety of instruments. In this disclosure, discussion will generally be limited to mouthpieces (301) which are designed to operate with delivery devices (303) whether specific or universal in nature. As discussed above, these devices (303) generally have a higher risk of fouling because so much more of the breath, and thus suspended particles and liquids, is provided to the testing chamber (331). However, all the principles, systems, and methods discussed herein can also be used on mouthpieces (201) for use with sampling devices (203). Further, this discussion will not get into the operation of check valves, and sanitation issues related thereto, since the presence or absence of such structures don't effect the operation of the trap (400). One of ordinary skill in the art would understand how the trap (400) can be incorporated with check valves and sanitation systems and methods.

Figure 4:
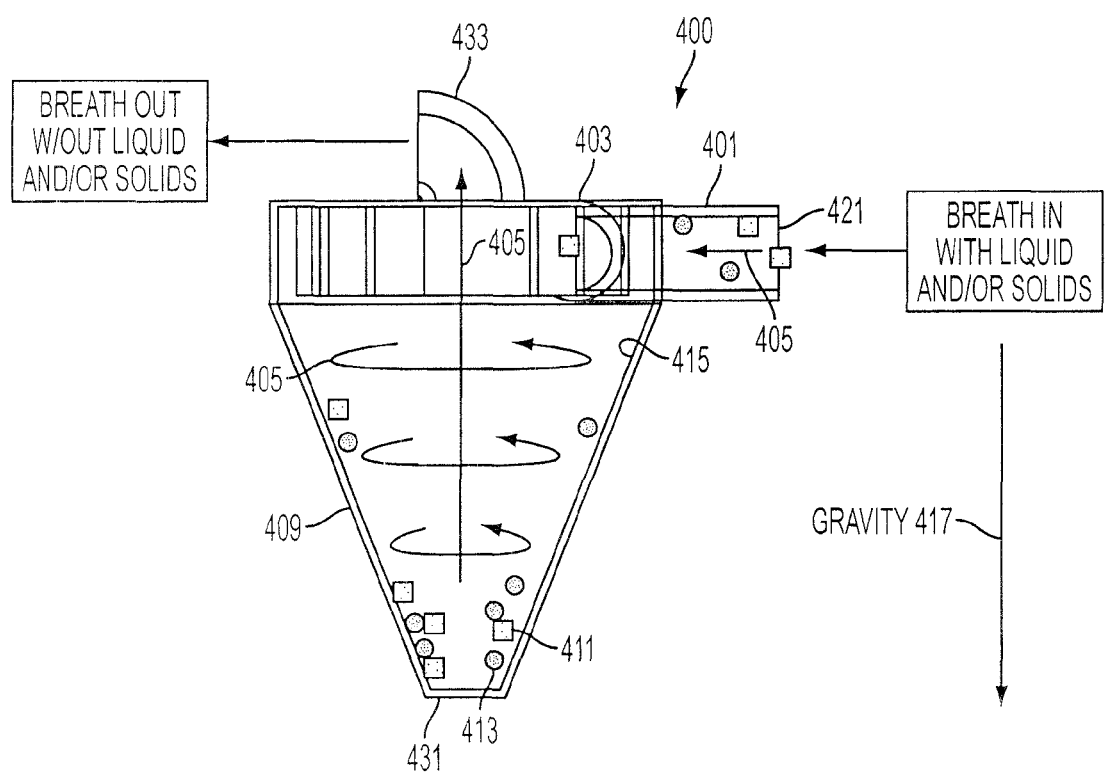
FIG. 4 shows a cross sectional view of an embodiment of a cyclonic separator which may be part of a mouthpiece or placed between a mouthpiece and a testing device.
Figure 5:
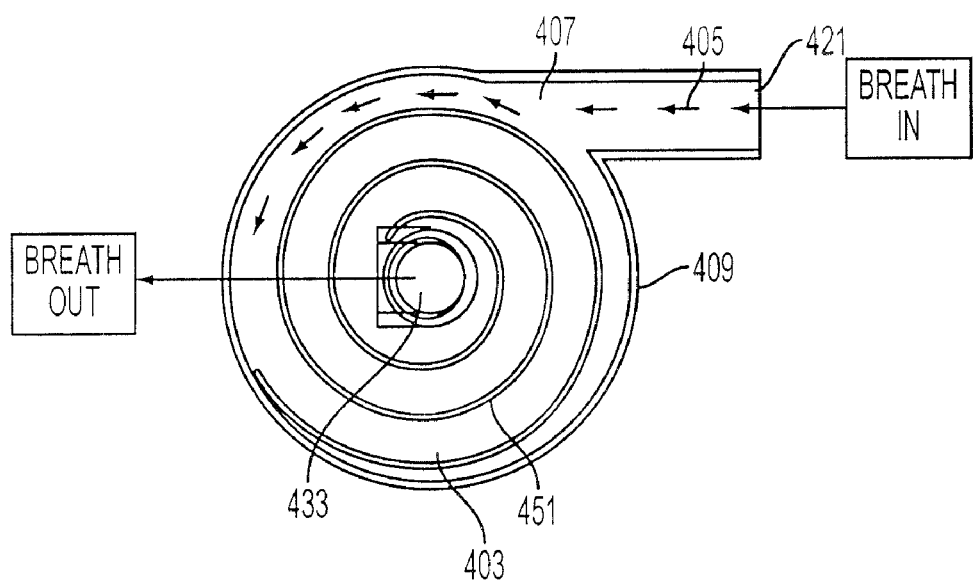
FIG. 5 shows a top view of the embodiment of FIG. 4 including circular baffling.

The embodiment of a trap (400) shown in FIGS. 4 and 5 provides for a cyclonic separator to separate liquids and solids from the breath stream and prevent their migration of such materials into a breath-measuring instrument (203) or (303) during a subject blow.

In the depicted embodiment, the trap (400) is designed to set up a circular flow pattern of breath within the trap (400). Generally the airflow (401) will be directed into the trap (400)

through a breath tube (401). This tube (401) may comprise the mouthpiece (301) for the device (303) which would operate similar to existing mouthpieces (301) where a user will place this tube (401) into their mouth, seal their lips around it, and blow into the tube (401). Alternatively, a disposable mouthpiece (such as mouthpiece (301)) may be attached into the input end (421) of the tube (401), interposing the trap (400) between the mouthpiece (301) and the device (303).

The tube (401) is positioned generally tangentially to the interior surface of the trap (400) towards the top (403). The breath flow (405) will enter the trap (400) through an inlet (407) into the trap (400). The trap (400) will generally be comprised of a main body portion (409) generally in the shape of an inverted cone. Generally, this shape will be a conical frustum, but need not be. Thus, air entering in tangential relation to the main body (409) will be directed around the internal surface of the body forming a vortex or cyclone within the main body (409).

As shown in FIG. 5, the inlet (407) will be arranged to provide the flow generally tangentially into the widest portion of the main body (409), which will be arranged on the mouthpiece so that it is generally at the top (403). The trap's (400) shape combined with the airflow inlet geometry will induce the breath flow (405) to spin creating a vortex or cyclone within the trap (400) in a fashion generally understood by those of ordinary skill in the art. Due to the rotation of the air stream (405), solid particles (411) and liquid droplets (413) suspended in the air stream (405) experience a centrifugal force causing them to move outward toward the interior wall (41.5) of the main body (409). Particles (411) and droplets (413) reaching the interior wall (415) of the trap (400) are driven downward by the force of gravity (417) and by the drag force from the downward component of the air flow (405). As the flow (405) approaches the bottom (431), the rotation of the air flow (405) will accelerate leading to higher centrifugal forces causing smaller and smaller particles (411) and droplets (413) to be forced from the flow (405) towards the edge and downward and further forcing larger particles (411) and droplets (413) previously forced from the air flow (405) to continue their downward motion.

As the cyclonic flow (405) approaches the bottom (431) it begins to turn in on itself and travel up through the center of the cyclone, eventually to exit out the top (403) through the exhaust tube (433) which is located in a generally central location in the widest portion of the conical main body (409). This change from a downward cyclonic flow to an upward cyclonic flow is caused by the relatively lower static pressure maintained in the center of the cyclone and in the exhaust tube (433). This flow reversal is generally completed inside the cyclone formed in the trap (400) and serves to send the air flow from the trap (400) and out the exhaust port (433).

Particles (411) and droplets (413) that have been centrifuged out to the interior surface (415) of the trap (400) are moved down by the force of gravity and by the drag force from the downward component of the airflow. Smaller particles are carried in the cyclonic flow (405) until they too are forced by increasing angular velocity. While some of these smaller particles centrifuge out of the flow (405), the smallest remain suspended in the flow and travel back up through the center of the cyclone to be exhausted through exhaust port (433). This action upon the particles (411) and droplets (413) traveling through the trap (400) therefore serves to collect larger particles at the base of the trap (400) while generally still inhibiting the smallest particles (such as the alcohol vapor in the breath) from being removed.

Because of the slanted sides of the main body (409), gravity also tends to cause liquids (413) to condense and slide down to the bottom of the main body (409) where they become trapped against the side and bottom (431) by the highest angular velocities. Therefore, with the trap (400) being unheated, liquid which condenses inside the trap (400) will generally not be pushed through the exhaust port (433) by the air flow (405), but will instead flow downward and collect. Alternatively, liquid condensation may become stuck to the sides of the main body (409) and, because of surface tension, may also serve to grab additional particles (411) or liquid (413) as it contacts it. Regardless, liquids (413) and particles (411) are generally removed from the breath while small vaporized matter, which is of interest in determining breath alcohol concentration, will exit the main body (409) at the top (403), far from where the liquids and solids are trapped at the bottom (431).

As shown in the embodiment of FIG. 5, circular, helical, or other shaped baffles (451) may be arranged toward the top (403) of the trap (400) to help set up the cyclonic flow and help ensure that any liquids (413) and/or solids (411) migrate to the bottom (431) before there is any chance they could exit the top (403). Because both the input (421) and exhaust (433) ports are relatively close to each other, there is some concern that with a stronger breath being provided particles (411) or (413) could be forced into the exhaust stream from the input stream breaking the cyclonic flow. While this is a relatively minimal concern, the presence of baffles (451) can further inhibit suspended liquids (413) and particles (411) from entering the exhaust port (433) and create additional surfaces for condensation and particle separation. These baffles (451), however, are not necessary and need not be included in alternative embodiments.

Those skilled in the art would understand that whether a check valve is added or not, or whether the mouthpiece (301) and/or trap (400) is disposable or not, the action of the cyclone is not affected. Thus the trap (400) may be provided as a part of the disposable mouthpiece (301), may be a component placed between the mouthpiece (301) and the inlet port (361) of the detector which may be emptied or washed at regular intervals or separately disposable, or may be semi-reusable, allowing for a certain build up of material from multiple tests before it is itself discarded and replaced in routine maintenance. In a reusable embodiment, the bottom (431) may include a drain port, release valve, or similar object to allow for liquids and/or solids to be removed between uses.

As should be clear, the trap (400) operation is independent of the type of sensor technology, and is applicable in any instance where a constituent in breath is to be measured and there is a need or desire to remove any liquids (413) and/or solids (411) from that breath before the breath vapor passes a given point in the path of the breath stream as it may be placed anywhere prior to the inlet port (361) of the detecting apparatus (303). Further, the trap (400) may be part of the mouthpiece (301) or may be provided separately and used in conjunction with any currently available mouthpieces (301) that are capable of interfacing with it. By forming tube (401) to provide a similar connection to input (361) this can enable the trap (400) to interface with most mouthpieces (301). Similarly, use of a universal connector on exhaust port (433), or a connector placed between the exhaust port and input (361), the trap (400) can be designed to operate with virtually any tester (303). In these situations, a traditional mouthpiece (301) will generally be inserted into the entrance port (421) of the trap (400) instead of this input port (421) acting as the mouthpiece (301) itself.

While the invention has been disclosed in connection with certain preferred embodiments, this should not be taken as a limitation to all of the provided details. Modifications and variations of the described embodiments may be made without departing from the spirit and scope of the invention, and other embodiments should be understood to be encompassed in the present disclosure as would be understood by those of ordinary skill in the art.

The invention claimed is:

1. A breath tester for trapping particles, the tester comprising:
    a trap including:
        an inverted generally conical frustum having a top and a bottom where the diameter of the top is greater than the diameter of the bottom and trapped particles are collected in the bottom;
        an inlet port arranged toward said top of said frustum, for having a breath flow enter said frustum and form a cyclone therein; and
        an exit port arranged at said top for exhausting breath flow from said conical frustum;
    a series of baffles arranged at the top of the inverted conical frustum flush with the inlet for aiding in establishing the cyclone and the migration of particles to the bottom of the trap;
    a sample inlet port for accepting a sample of an exhausted breath vapor from said exit port; and
    a detector, which can determine the alcohol concentration of said sample.

2. The tester of claim 1 wherein said detector is a fuel cell.

3. The tester of claim 1 wherein said detector utilizes infrared absorption.

4. The tester of claim 1 wherein said tester is a delivery tester.

5. The tester of claim 1 wherein said breath flow is produced by a human being.

6. The tester of claim 1 wherein said breath flow is directly provided to said detector.

7. The tester of claim 1 wherein liquid suspended in said breath flow at least partially condenses from said breath flow on an inner surface of said frustum.

8. The tester of claim 1 wherein said trap is disposable after each use.

9. The tester of claim 1 wherein said trap is used for multiple uses.

10. The tester of claim 1 wherein said exit port is generally centered in said top.

11. The tester of claim 1 wherein said trap further comprises baffles inside said inverted conical frustum.

12. The tester of claim 11 wherein said baffles are generally circular.

13. The tester of claim 11 wherein said baffles are generally helical.

14. A method of providing a breath stream for breath alcohol analysis, the method comprising:
    having a user breathe a breath flow into an input tube;
    inducing a cyclone on said breath flow within a trap by said breath flow coming into contact with a series of baffles flush with the inlet arranged at the top of the inverted conical frustum;
    utilizing said cyclone to expel at least some solid particles and liquid droplets from said breath flow;
    expelling said breath flow from said trap while capturing said particles and droplets in said trap; and
    providing said expelled breath flow to a breath alcohol testing device.

15. The method of claim 14 wherein said breath alcohol testing device is a delivery type of device.

16. The method of claim 14 wherein said breath alcohol testing device utilizes infrared absorption on said expelled breath flow.

17. The method of claim 14 wherein said trap comprises an inverted conical frustum.

18. The method of claim 17 wherein said trap further comprises baffles.

* * * * *